United States Patent
Qu et al.

(10) Patent No.: US 11,030,324 B2
(45) Date of Patent: Jun. 8, 2021

(54) PROACTIVE RESISTANCE TO RE-IDENTIFICATION OF GENOMIC DATA

(71) Applicant: KONINKLIJKE PHILIPS N.V., Eindhoven (NL)

(72) Inventors: Jin Qu, Shanghai (CN); Fubiao Xia, Shanghai (CN); Yong Mao, Hawthorne, NY (US); Alexander Ryan Mankovich, Boston, MA (US); Raymond J. Krasinski, Suffern, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 264 days.

(21) Appl. No.: 16/199,765

(22) Filed: Nov. 26, 2018

(65) Prior Publication Data

US 2019/0163918 A1    May 30, 2019

(30) Foreign Application Priority Data

Nov. 30, 2017  (WO) ............... PCT/CN2017/113863
Jan. 30, 2018  (EP) .................................. 18154200

(51) Int. Cl.
*G06F 21/57* (2013.01)
*G06F 21/62* (2013.01)
(Continued)

(52) U.S. Cl.
CPC ........ *G06F 21/577* (2013.01); *G06F 16/2455* (2019.01); *G06F 21/6218* (2013.01);
(Continued)

(58) Field of Classification Search
CPC .......................... G06F 21/577; G06F 21/6218
See application file for complete search history.

(56) References Cited

U.S. PATENT DOCUMENTS 6,640,211 B1 * 10/2003 Holden ............... G06Q 20/382
                                                              705/64
6,968,385 B1 * 11/2005 Gilbert ............... G06F 21/6218
                                                              709/229
(Continued)

OTHER PUBLICATIONS

Anonymous: "Privacy in Genomics", National Human Genome Research Institute, https://www.genome.gov/27561246/privacy-in-genomics/, 3 pages (Abstract).
(Continued)

*Primary Examiner* — Jason Chiang

(57) ABSTRACT

A method for assessing risk associated with a request from an inquirer for allele frequency from a database of genetic data, comprising: (i) generating an allele database comprising allele frequency information and request frequency information for each of a plurality of alleles; (ii) generating an inquirer database comprising allele request information about a plurality of inquirers; (iii) receiving a request for genetic data from an inquirer, comprising a request for allele frequency for one or more alleles and an identifier of the inquirer; (iv) updating the request frequency information based on the received request; (v) updating the allele request information for the requesting inquirer; (vi) calculating an allele risk score; (vii) calculating an inquirer risk score; and (viii) assessing, based on the allele risk score and the inquirer risk score, a risk associated with the received request.

15 Claims, 2 Drawing Sheets

(51) Int. Cl.
*G06F 16/2455* (2019.01)
*G16B 50/00* (2019.01)
*G16H 10/60* (2018.01)
*G06Q 50/26* (2012.01)

(52) U.S. Cl.
CPC ........... *G06Q 50/265* (2013.01); *G16B 50/00* (2019.02); *G16H 10/60* (2018.01); *G06F 2221/034* (2013.01)

(56) References Cited

U.S. PATENT DOCUMENTS

| | | | | |
|---|---|---|---|---|
| 9,942,206 B1* | 4/2018 | Miller | .................... | H04L 9/3239 |
| 10,438,244 B2* | 10/2019 | Nelson | .................... | G16H 40/63 |
| 2002/0095585 A1* | 7/2002 | Scott | .................... | G06Q 10/10 |
| | | | | 713/185 |
| 2003/0033168 A1* | 2/2003 | Califano | .................... | G16H 10/60 |
| | | | | 705/3 |
| 2003/0046114 A1* | 3/2003 | Davies | .................... | G06F 19/00 |
| | | | | 705/3 |
| 2003/0055824 A1* | 3/2003 | Califano | ............... | G06F 21/6263 |
| 2005/0026117 A1* | 2/2005 | Judson | .................... | G16H 70/40 |
| | | | | 434/154 |
| 2007/0061085 A1* | 3/2007 | Fernandez | ............. | G06Q 50/22 |
| | | | | 702/20 |
| 2008/0261220 A1* | 10/2008 | Cracauer | ................. | C12P 19/34 |
| | | | | 435/6.11 |
| 2009/0094059 A1* | 4/2009 | Coleman | ................ | G06Q 50/22 |
| | | | | 705/3 |
| 2010/0121872 A1* | 5/2010 | Subramaniam | ........ | G16B 50/00 |
| | | | | 707/769 |
| 2010/0169107 A1* | 7/2010 | Ahn | ........................ | G16B 50/00 |
| | | | | 705/1.1 |
| 2010/0169365 A1* | 7/2010 | Chupp | ................... | G06F 16/332 |
| | | | | 707/769 |
| 2011/0238482 A1* | 9/2011 | Carney | ............... | G06F 21/6245 |
| | | | | 705/14.36 |
| 2013/0096943 A1* | 4/2013 | Carey | ................. | G06F 21/6263 |
| | | | | 705/2 |
| 2014/0350968 A1* | 11/2014 | Hahn | ..................... | G16B 50/00 |
| | | | | 705/3 |
| 2015/0127378 A1* | 5/2015 | Downs | ................... | G16H 10/60 |
| | | | | 705/3 |
| 2015/0317490 A1* | 11/2015 | Carey | .................... | G16B 50/00 |
| | | | | 726/26 |
| 2016/0055499 A1* | 2/2016 | Hawkins | ............ | G06Q 30/0271 |
| | | | | 705/7.33 |
| 2016/0239891 A1* | 8/2016 | Braghetto Neto | .......................... | |
| | | | | G06Q 30/0201 |
| 2017/0024582 A1* | 1/2017 | Fiume | ..................... | H04L 63/08 |
| 2017/0230406 A1* | 8/2017 | Gould | .................. | G06F 21/552 |
| 2017/0235971 A1* | 8/2017 | Kline | .................... | G16B 30/00 |
| | | | | 713/193 |
| 2017/0337487 A1* | 11/2017 | Nock | ........................ | G06N 3/08 |
| 2018/0046753 A1* | 2/2018 | Shelton | ................. | G16B 20/00 |
| 2018/0365446 A1* | 12/2018 | Alves De Carvalho | ..................... | |
| | | | | G16H 10/60 |
| 2020/0042735 A1* | 2/2020 | Baluch | .................. | G16B 30/20 |

OTHER PUBLICATIONS

Gymrek, et al., "Identifying Personal Genomes by Surname Inference", Science, vol. 339, Jan. 18, 2013, pp. 321-324.

* cited by examiner

PROACTIVE RESISTANCE TO RE-IDENTIFICATION OF GENOMIC DATA

CROSS-REFERENCE TO RELATED APPLICATION

The present application claims priority and the benefit of International Application Serial No. PCT/CN2017/113863, filed Nov. 30, 2017, and of European Application Serial No. 18154200.2, filed Jan. 30, 2018, which are hereby incorporated by reference in their entirety.

FIELD OF THE INVENTION

The present disclosure is directed generally to methods and systems for assessing risk associated with requests for information from a database of genetic sequences.

BACKGROUND

By sharing and comparing the genotypes of millions of individuals, clinicians and researchers can better predict the clinical impact of genetic variants, make links between rare disease cases, better understand genotype-phenotype correlations, and develop novel treatment. Accordingly, there are solutions that enable the sharing of genomic and clinical data.

The Beacon Project from the Global Alliance for Genomics and Health is just one example of such a solution. This project allows researchers to query a database of genetic sequences for information about a specific allele. This mitigates risk by preventing re-identification of the individual that provided a genetic sequence, although the solution may also optionally disclose additional metadata associated with the queried allele such as allele frequencies, pathogenicity scores, and associated phenotypes, among other data.

Although rare alleles often prove to be particularly interesting to researchers, these rare alleles also increase the probability or ease of re-identification. Accordingly, these databases may be vulnerable to re-identification attacks such as attribute disclosure attacks and attacks in which the attacker queries for a large number of variants.

An attribute disclosure attack is a re-identification attack in which the attacker attempts to determine whether sensitive attributes about an individual can be inferred through attributes disclosable from the database of genetic sequences, such as HIV status and/or mental health status, and typically requires some prior attribute information.

The attacker querying for a large number of variants is attempting to determine whether the database of genetic sequences comprises a specific genomic sequence, based on prior knowledge or suspicion of the genetic sequence. Unfortunately, models for population allele frequencies can be leveraged to reduce the number of queries required in such an attack. Although a threshold may be set for the number of queries to the database of genomic sequences, setting the threshold too low may enable attackers with previous information to obtain sufficient genetic information, and setting the threshold too high may block valid researchers.

SUMMARY OF THE INVENTION

There is a continued need for improved assessment of risk associated with queries to databases of genetic sequences.

The present disclosure is directed to inventive methods and systems for assessing risk associated with a request for information from a database of genetic sequences. Various embodiments and implementations herein are directed to a system including an allele database comprising allele frequency information and request frequency information for each of a plurality of alleles, and an inquirer database comprising allele request information about a plurality of inquirers. The system receives a request for genetic data from an inquirer which includes a request for allele frequency for at least one allele, and an identifier of the inquirer. The system updates the allele database and the inquirer database based on the received request, and calculates an allele risk score based on the updated allele database, and an inquirer risk score based on the updated inquirer database. The system can then assess, based on the allele risk score and the inquirer risk score, a risk associated with the received request.

Generally in one aspect, a method for assessing risk associated with a request from an inquirer for allele frequency from a database of genetic data is provided. The method includes the steps of: (i) generating an allele database comprising allele frequency information and request frequency information for each of a plurality of alleles, wherein the allele frequency information is extracted from a plurality of genetic sequences, and wherein the request frequency information comprises, for each of the plurality of genetic sequences, a count of previous requests for information about each of the plurality of alleles found within a respective genetic sequence; (ii) generating an inquirer database comprising allele request information about a plurality of inquirers, wherein the allele request information comprises information about allele frequency information previously requested by each of a plurality of inquirers; (iii) receiving a request for genetic data from an inquirer, comprising a request for allele frequency for one or more alleles and an identifier of the inquirer; (iv) updating in the allele database, for each of the plurality of genetic sequences comprising the one or more alleles, the request frequency information based on the received request; (v) updating in the inquirer database, based on the received inquirer identifier, the allele request information for the requesting inquirer; (vi) calculating an allele risk score based on the updated allele database; (vii) calculating an inquirer risk score based on the updated inquirer database; and (viii) assessing, based on the allele risk score and the inquirer risk score, a risk associated with the received request.

According to an embodiment, the step of assessing a risk associated with the received request comprises the steps of: (i) summing the calculated allele risk score and inquirer risk score to generate a total risk assessment score; and (ii) comparing the total risk assessment score to a predetermined threshold.

According to an embodiment, the method further includes the step of allowing the request for genetic data from the inquirer if the risk associated with the received request is assessed to be below a predetermined threshold.

According to an embodiment, the method further includes the step of denying the request for genetic data from the inquirer if the risk associated with the received request is assessed to be above a predetermined threshold.

According to an embodiment, the method further includes the step of reporting the risk associated with the received request.

According to an embodiment, the allele risk score is calculated using the equation:

$$Ri = \sum_{j=1}^{n} \text{Index}(i, j)/F(j)$$

where Ri is the risk level of the genetic sequence, n is the number of rare alleles, F(j) is the frequency of allele j, and Index (i,j) is the number of requests for allele j for genetic sequence i.

According to an embodiment, the inquirer risk score is calculated using the equation:

$$Dj = \sum_{k=1}^{m} \left( \sum_{i=1}^{n} (\text{Index}(i, j)/Fi) \right) Rk$$

where Dj is the risk level for an inquirer j, m is the genetic sequence, n is the number of rare alleles, Index (i,j) is the number of requests for allele j for genetic sequence i, F(i) is the frequency of allele i, and Rk is the risk level.

According to an embodiment, the method further includes the step of requesting additional identifying information from the inquirer.

According to an aspect is a risk assessment system configured to assess risk associated with a request from an inquirer for allele frequency from a database of genetic data. The system includes: (i) an allele database comprising allele frequency information and request frequency information for each of a plurality of alleles, wherein the allele frequency information is extracted from a plurality of genetic sequences, and wherein the request frequency information comprises, for each of the plurality of genetic sequences, a count of previous requests for information about each of the plurality of alleles found within a respective genetic sequence; (ii) an inquirer database comprising allele request information about a plurality of inquirers, wherein the allele request information comprises information about allele frequency information previously requested by each of a plurality of inquirers; and (iii) a processor configured to receive a request for genetic data from an inquirer, comprising a request for allele frequency for one or more alleles and an identifier of the inquirer, the processor comprising: an allele database generator configured to update, in the allele database for each of the plurality of genetic sequences comprising the one or more alleles, the request frequency information based on the received request; an inquirer database generator configured to update, in the inquirer database based on the received inquirer identifier, the allele request information for the requesting inquirer; and a risk analyzer configured to: calculate an allele risk score based on the updated allele database; (ii) calculate an inquirer risk score based on the updated inquirer database; and (ii) assess, based on the allele risk score and the inquirer risk score, a risk associated with the received request.

According to an embodiment, the system further includes a user interface configured to report the assessed risk.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a system and method for assessing the risk associated with providing allele data from a database of genetic sequences. More generally, Applicant has recognized and appreciated that it would be beneficial to provide a system that mitigates risk by determining whether to provide requested allele data to an inquirer. The system comprises an allele database comprising allele frequency information and request frequency information for each of a plurality of alleles, and an inquirer database comprising allele request information about a plurality of inquirers. When the system receives a request for genetic data from an inquirer which includes a request for allele frequency and an identifier of the inquirer, the allele database and inquirer database are updated. The system then calculates an allele risk score based on the updated allele database, and an inquirer risk score based on the updated inquirer database. The system then assesses, based on the allele risk score and the inquirer risk score, a risk associated with the received request.

Figure 1:
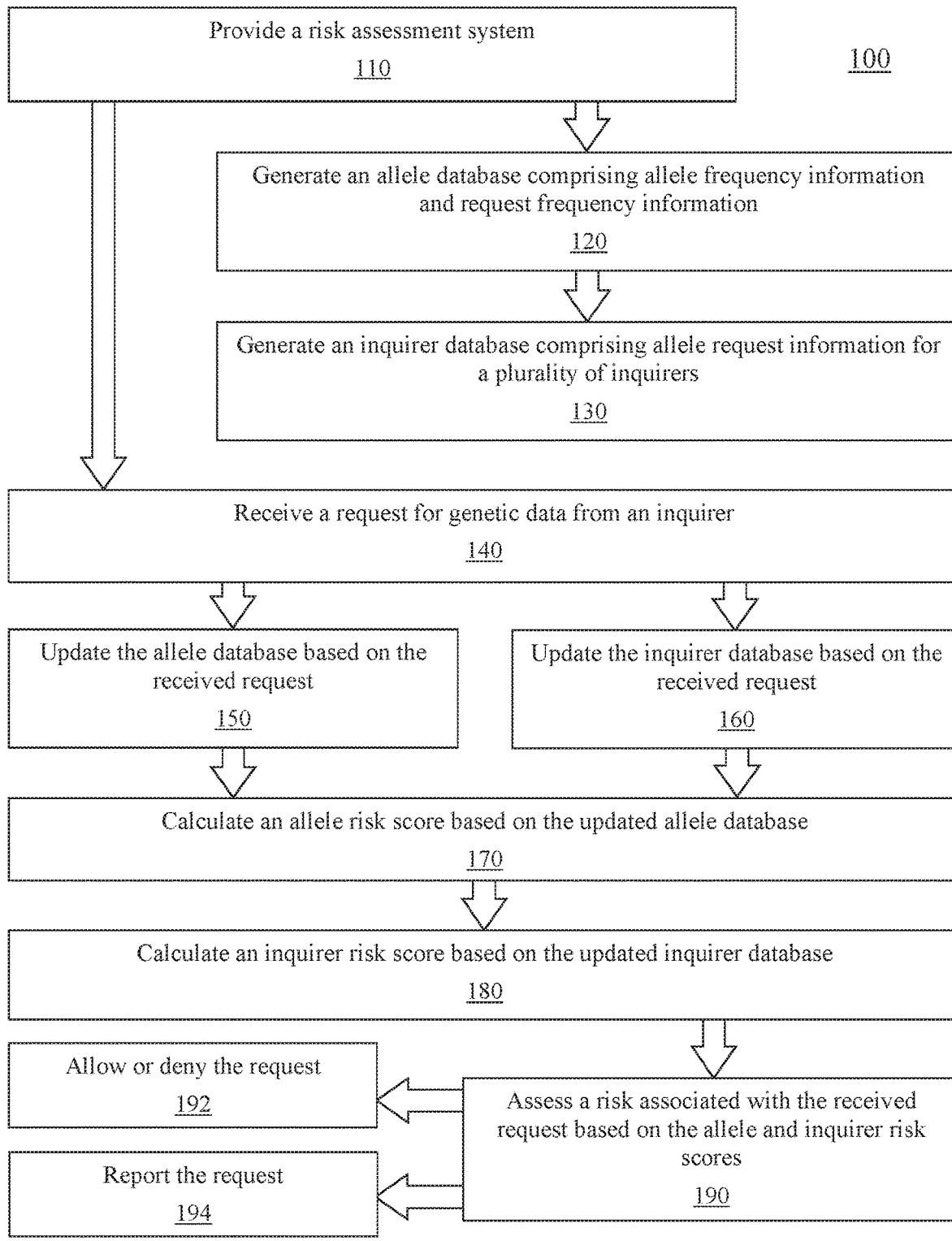
FIG. 1 is a flowchart of a method for assessing risk associated with a request from an inquirer for allele frequency from a database of genetic data, in accordance with an embodiment.

Referring to FIG. 1, in one embodiment, is a flowchart of a method 100 for assessing risk associated with a request from an inquirer for allele frequency from a database of genetic data. At step 110 of the method, a risk assessment system is provided. The risk assessment system may be any of the systems described or otherwise envisioned herein.

At step 120 of the method, an allele database is generated. The allele database includes allele frequency information which is extracted from a plurality of genomic sequences. The allele database also includes request frequency information for each of the alleles in the database. The request frequency information includes a count of previous requests for information about the respective allele.

The allele frequency information is information about the occurrence frequency of an allele, or a variation of a gene or DNA sequence, in a collection of one or more genetic sequences. For example, the allele frequency information may comprise the frequency of single-nucleotide polymorphisms (SNPs) within genetic sequences found within the collection or database of sequences. The genetic sequences may be whole genome sequences and/or partial sequences such as an exome or individual genes or other genomic regions.

As just one example, if the database comprises a plurality of genetic sequences and the relative frequency of the C allele to the T allele at rs1805007 is 9:1 within the database, the frequency of the C allele of rs1805007 is 90% or 0.9 and the frequency of T allele of rs1805007 is 10% or 0.1. When a new genetic sequence is added to the collection, the genetic sequence is analyzed for its allele value at rs1805007 (in addition to one or more other locations), and the allele frequency information for rs1805007 in the allele database is updated. The genetic sequences and the allele frequency information may be stored in the same or different databases. For example, the genetic sequences may be stored in one or more remote databases, and the compiled allele frequency information may be stored in a single local or remote database, although multiple databases are possible.

According to an embodiment, the allele frequency information and the request frequency information are stored in a database table or other storage medium. Referring to Table 1, for example, is an embodiment of an allele frequency table. In this table, there are m genetic sequences (Genetic sequence 1, 2, i, ... m) and n alleles (Allele 1, 2, j, ... n). An allele frequency F(1, 2, j, ... n) is provided for each allele.

TABLE 1

Allele Frequency Table

|  | Allele 1 | Allele 2 | Allele j | ... | Allele n |
|---|---|---|---|---|---|
| Genetic sequence 1 | | | Index(1, j) | | |
| Genetic sequence 2 | | | | | |
| Genetic sequence i | | | Index(i, j) | | |
| ... | | | | | |
| Genetic sequence m | | | Index(m, j) | | |
| Allele frequency | F(1) | F(2) | F(j) | ... | F(n) |

Table 1 also comprises request frequency information, including a count of previous requests for information about the respective allele. In Table 1, the index for each allele in each genome indicates the count of previous requests for information about that allele. The index for each allele is set to "0" until it is queried. When allele j is queried, for example, the index of every genetic sequence containing allele j is changed to "1" while the index of ever genetic sequence that doesn't contain allele j remains at "0." When allele j is next queried again, the index of every genetic sequence containing allele j is changed from "1" to "2" while the index of ever genetic sequence that doesn't contain allele j remains at "0." In this way, the system tracks the count of requests for information about each allele. Similarly, the system tracks the number of alleles each genetic sequence has reported.

At step 130 of the method, an inquirer database is generated. The inquirer database includes allele request information about a plurality of inquirers, including information about allele frequency information previously requested by each of the inquirers. The inquirer database may be stored in the same database as the allele frequency information and/or genetic sequences, or may be stored remote from the databases comprising the allele frequency information and/or genetic sequences. The inquirer information may be stored in a single local or remote database, although multiple databases are possible.

The information about inquirers stored within the inquirer database can include any identifying information about an individual or entity, real or automated, submitting a query to the risk assessment system. The system may collect identifying information such as an IP address, email address, name, phone number, coordinates or location, address, institutional or research facility association, credentials, and/or any other identifying or potentially identifying information. The allele frequency information stored within the inquirer database can include information about the occurrence frequency of one or more alleles in a collection of genetic sequences. The inquirer database further includes information about allele frequency information previously requested by inquirers. The inquirer database tracks, using any method, the alleles requested by an inquirer, which is utilized for subsequent risk assessment.

According to an embodiment, the information about inquirers and inquirer queries are stored in a database table or other storage medium. Referring to Table 2, for example, is an embodiment of an inquirer query table. In this table, there are m genetic sequences, n alleles (Allele 1, 2, i, ... n), and q inquirers (Inquirer 1, 2, j, ... q). An allele frequency F(1, 2, i, ... n) is provided for each allele.

TABLE 2

Inquirer Query Table

| | Allele frequency | Inquirer 1 | Inquirer 2 | ... | Inquirer j | ... | Inquirer q |
|---|---|---|---|---|---|---|---|
| Allele 1 | F1 | Index (1, 1) | | | | | |
| Allele 2 | F2 | | | | | | |
| ... | | | | | | | |
| Allele i | F(i) | | | | Index (i, j) | | |
| ... | | | | | | | |
| Allele n | F(n) | | | | | | |

Table 2 also comprises request frequency information, including a count of previous requests for information about a respective allele. In contrast with Table 1, a count of previous requests for information about each respective allele is maintained for each inquirer. The index for each allele for each inquirer is set to "0" until it is queried by that inquirer. When inquirer j queries allele i, for example, the index for inquirer j at allele i is changed to "1" to reflect the request. When inquirer 1 queries allele 1, the index for inquirer 1 at allele 1 is changed to "1" to reflect the request.

At step 140 of the method, the risk assessment system receives a request for information from an inquirer. The request for information comprises a request for allele frequency for one or more alleles, and preferably comprises identifying information about the inquirer. The request for information can be a query submitted to the risk assessment system directly, or can be submitted to a database of genetic sequences and intercepted by, diverted to, or re-routed to the risk assessment system as a security measure. The inquirer can be a person submitting a request via a local or remote user interface, or can be a computer or other automated or computerized entity that is programmed or otherwise directed to query the database of genetic information. The request may be submitted either locally or remotely, and can be made via wireless and/or wired communication. According to an embodiment, the database of genetic information comprises an API or other portal, gateway, or interface that allows inquirers to request information.

The request for information comprises a request for allele frequency for one or more alleles. For example, the query may comprise a list of alleles, SNPs, and/or genomic locations for which allele frequency information is requested. A researcher may wish to know the frequency of allele A at rs1805007. Accordingly, the request may comprise a reference SNP ID number, a chromosomal location, and/or any other information.

The request for information comprises inquirer information about the inquirer. For example, the request may comprise identifying information such as an IP address, email address, name, phone number, coordinates or location, address, institutional or research facility association, credentials, and/or any other identifying or potentially identifying information.

At step 150 of the method, the allele database is updated based on the one or more alleles identified in the received request for information. The request frequency for each of the one or more alleles identified in the received request for information is increased to reflect the latest request. Referring to Table 1, for example, if allele j is queried, the index of every genetic sequence containing allele j is changed to "1" while the index of ever genetic sequence that doesn't contain allele j remains at "0."

At step 160 of the method, the inquirer database is updated based on the inquirer information provided in or by the received request for information. The request frequency for each of the one or more alleles identified in the received request for information, for the requesting or querying inquirer, is increased to reflect the latest request. Referring to Table 2, for example, if inquirer j queries allele i, for example, the index for inquirer j at allele i is changed to "1" to reflect the request.

At step 170 of the method, the risk assessment system calculates an allele risk score based on the updated allele database. The allele risk score is based on the frequency of the allele among all the sequences in the allele database. Accordingly, although an allele may be very rare in the general public, it may be common in the allele database and thus there is a low allele risk score. Similarly, although an allele may be very common in the general public, it may be rare in the allele database and thus there is a high allele risk score.

A risk manager of the risk assessment system determines a risk level for a particular sequence in the database of genetic information based on the requested information, allele frequency, and/or history of requests for that particular sequence. The lower the frequency of an allele, the larger the probability that the genomic sequence(s) containing that allele could be re-identified. Thus, the reciprocal of an allele frequency can be used to express the possibility of re-identifying a sequence. According to an embodiment, the risk level for a genetic sequence in the database is calculated using Equation 1:

$$Ri = \sum_{j=1}^{n} \text{Index}(i, j)/F(j) \qquad (\text{Eq. 1})$$

where Ri is the risk level of the ith genetic sequence, n is the number of rare alleles, F(j) is the frequency of allele j, and Index (i,j) is the number of requests for allele j for genetic sequence i.

The allele database can track the risk level for each genetic sequence m. Referring to Table 3, for example, is an allele table in which each genetic sequence m comprises a Risk Level R(m) for that genetic sequence based on the allele frequencies for that genetic sequence, as well as on the number of requests for allele frequencies for alleles found within that genetic sequence. This Risk Level can be updated with each new request.

TABLE 3

Allele Frequency Table With Risk Level

| | Allele 1 | Allele 2 | Allele j | ... | Allele n | Risk Level |
|---|---|---|---|---|---|---|
| Genetic sequence 1 | | | Index (1, j) | | | R(1) |
| Genetic sequence 2 | | | | | | R(2) |
| Genetic sequence i | | | Index (i, j) | | | R(i) |
| ... | | | | | | ... |

TABLE 3-continued

Allele Frequency Table With Risk Level

|  | Allele 1 | Allele 2 | Allele j | ... | Allele n | Risk Level |
|---|---|---|---|---|---|---|
| Genetic sequence m |  |  | Index (m, j) |  |  | R(m) |
| Allele frequency | F(1) | F(2) | F(j) | ... | F(n) |  |

According to an embodiment, the risk level may be modified based on one or more other pieces of internal and/or external information. For example, if information about a genetic sequence stored within the database of genetic information is available publicly or in another accessible database, the risk level for that genetic sequence is increased accordingly, as re-identification may be easier. For example, if all or a portion of an individual's genome is already available publicly or via an accessible database, an entity can more easily determine whether the individual's genome is stored within the database of genetic information by, for example, querying for known alleles.

At step 180 of the method, the risk assessment system calculates an inquirer risk score based on the updated inquirer database. The inquirer risk score is based on the number of alleles requested by the inquirer, as well as on the frequency of those alleles in the database.

A risk manager of the risk assessment system determines a risk level for a particular inquirer in the inquirer database or query table. According to an embodiment, the risk level for an inquirer in the database is calculated using Equation 2:

$$Dj = \sum_{k=1}^{m} \left( \sum_{i=1}^{n} (\text{Index}(i, j)/Fi) \right) Rk \qquad (\text{Eq. 2})$$

where Dj is the risk level for an inquirer j, m is the genetic sequence, n is the number of rare alleles, Index (i,j) is the number of requests for allele j for genetic sequence i, F(i) is the frequency of allele i, and Rk is the risk level.

The inquirer database can track the risk level for each inquirer q. Referring to Table 4, for example, is an inquirer table in which each inquirer (1, 2, j, . . . q) comprises a Risk Level D(q) for that inquirer based on allele frequencies for alleles that the inquirer has requested in this and any previous requests. The Inquirer Risk Level can be updated with each new request.

TABLE 4

Inquirer Query Table With Risk Level

|  | Allele frequency | Inquirer 1 | Inquirer 2 | ... | Inquirer j | ... | Inquirer q |
|---|---|---|---|---|---|---|---|
| Allele 1 | F1 | Index (1, 1) |  |  |  |  |  |
| Allele 2 | F2 |  |  |  |  |  |  |
| ... |  |  |  |  |  |  |  |
| Allele i | F(i) |  |  |  | Index (i, j) |  |  |
| ... |  |  |  |  |  |  |  |
| Allele n | F(n) |  |  |  |  |  |  |
| Risk Level |  | D1 |  | ... | Dj | ... | Dq |

According to an embodiment, the inquirer risk level may be modified based on one or more other pieces of internal and/or external information. For example, if information about an inquirer within the inquirer database is known, such as a high risk factor associated with an inquirer, the risk level for that inquirer may be increased accordingly. According to another embodiment, if the inquirer is new or unknown, or has not accessed or queried the database within a predetermined timeframe, the risk level for that inquirer may be increased accordingly. There may also be situations where the risk level for an inquirer is decreased, such as with two-factor verification, biometric verification, or other verification methods that increase the likelihood that an inquirer is valid and unlikely to be attempting to re-identify genetic sequences in the database.

At step 190 of the method, the risk assessment system assesses the risk associated with a received request for information from the database of genetic information. This assessment is based at least in part on the calculated allele risk score and the calculated inquirer risk score.

According to one embodiment, the calculated allele risk score and calculated inquirer risk score can comprise a total risk assessment score, which is the risk associated with the received request. For example, the sum may be the sum of the output of Equation 1 and Equation 2, although other methods of calculating the total risk assessment score are possible.

According to one embodiment, the sum of the allele risk score and the inquirer risk score is compared to one or more thresholds to determine the risk level. For example, the risk assessment system may comprise a continuum or a series of risk level values, such as no risk, low risk, moderate risk, and high risk values. If the sum of the allele risk score and the inquirer risk score meets and/or exceeds the high risk value, or the moderate risk value depending on the risk tolerance of the system, the risk assessment system may determine that the risk is too great and that the inquiry should be denied. If the sum of the allele risk score and the inquirer risk score falls below the high risk value, or the moderate risk value depending on the risk tolerance of the system, the risk assessment system may determine that the risk is acceptable and the inquiry should be allowed.

At step 192 of the method, the risk assessment system may implement the assessed risk by allowing or denying the received request for genetic information from the inquirer. For example, if the assessed risk is determined by the risk assessment system to be too great, the system will deny the received request. If the assessed risk is determined by the risk assessment system to be acceptable, the system will grant the received request. Denying or granting the received request may comprise allowing the query to proceed to the database or preventing the query from proceeding to the database. Similarly, denying or granting the received request may comprise preventing information retrieved from a query from being provided to the inquirer, or allowing the retrieved information to be provided to the inquirer. Accordingly, the request may be allowed or denied at any point in the query process.

As another option at step 192, the risk assessment system may request additional information from the inquirer in response to an assessed risk. For example, the risk assessment system may request information about the identity of the inquirer if the inquirer cannot be identified, or if the inquirer is identified as a high-risk inquirer, or if the inquirer is requesting information that triggers a high allele risk score. According to an embodiment, the risk assessment system may require that the inquirer register as a user of the system, and thus must provide sufficient identifying information.

At step 194, of the method, the risk assessment system may report the assessed risk. A report of assessed risk may be stored for analytics, reported immediately, and/or available upon request. The report may comprise information about the allele(s) requested, the inquirer's identity, the calculated allele risk score and inquirer risk score, the assessed risk level, time and date, and/or any other information. This information may be stored in a database, displayed on a user interface, provided in a printed report, or otherwise stored or provided. For example, the risk assessment system may immediately report an assessed risk level to an administrator of the risk assessment system. Reporting may be based in whole or in part on the assessed risk level. For example, reporting may be provided for every request, or may only be provided in response to high-risk requests or inquirers, among many other options.

Figure 2:
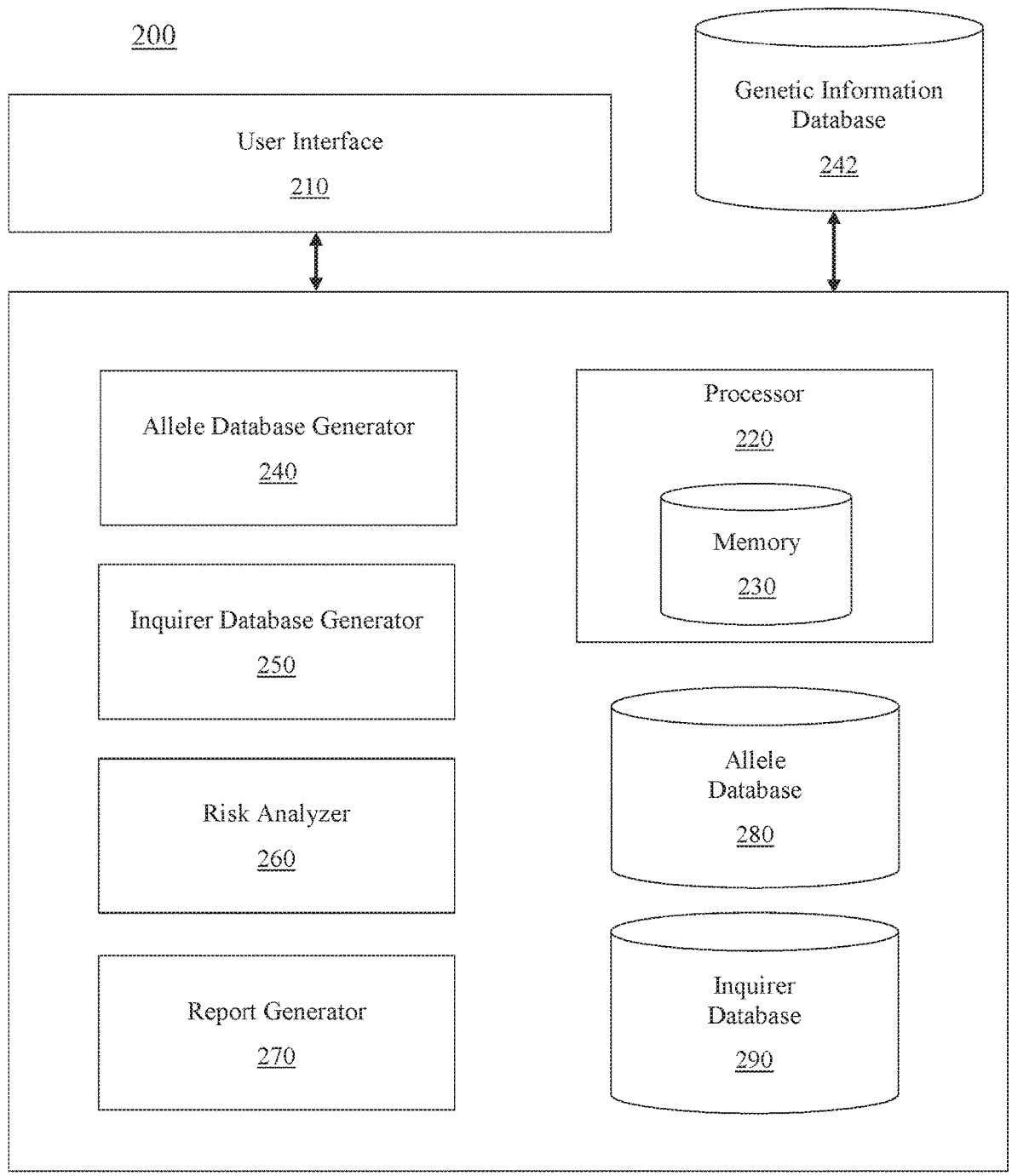
FIG. 2 is a schematic representation of a risk assessment system, in accordance with an embodiment.

Referring to FIG. 2, in one embodiment, is a schematic representation of a risk assessment system 200, such as a risk manager. System 200 can comprise any of the modules, elements, databases, processors, and/or other components described or otherwise envisioned herein.

According to an embodiment, system 200 comprises a user interface 210 to receive input from an administrator, and/or to provide information such as a risk assessment to an administrator. The user interface can be any device or system that allows information to be conveyed and/or received, such as a speaker or screen, among many other types of user interfaces. The information may also be conveyed to and/or received from a computing device or an automated system. The user interface may be located with one or more other components of the system, or may located remote from the system and in communication via a wired and/or wireless communications network.

According to an embodiment, system 200 comprises a processor 220 which performs one or more steps of the method, and may comprise one or more of the modules. Processor 220 may be formed of one or multiple modules, and can comprise, for example, a memory 230. Processor 220 may take any suitable form, including but not limited to a microcontroller, multiple microcontrollers, circuitry, a single processor, or plural processors. Memory 230 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by the processor, controls operation of one or more components of system 200.

According to an embodiment, system 200 comprises an allele database generator 240, which may be a processor, a component of one or more processors, and/or a software algorithm. Allele database generator 240 generates allele database 280 comprising allele frequency information extracted from a plurality of genomic sequences. The allele database also includes request frequency information for each of the alleles in the database, which includes a count of previous requests for information about the respective allele. As described or otherwise envisioned herein, the allele frequency information is information about the occurrence frequency of an allele, or a variation of a gene or DNA sequence, in a collection of one or more genetic sequences. The genetic sequences may be whole genome sequences and/or partial sequences such as an exome or individual genes or other genomic regions. The information provided in Tables 1 and 3 are just a few examples of the type of information, and structure of information, than can be included in allele database 280.

The allele database generator 240 generates allele database 280 using information from a plurality of genetic sequences, which may be whole genome sequences and/or partial sequences such as an exome or individual genes or other genomic regions. According to an embodiment, the genetic sequences are stored in a genetic information database 242, which may be a component of system 200, or may be remote from but in communication with system 200. For example, the allele database generator 240 may communicate via a wired and/or wireless communication link with genetic information database 242 in order to extract the allele frequency information from the genetic sequences stored in the genetic information database.

According to an embodiment, allele database generator 240 also updates allele database 280 in response to a request for information from an inquirer. The request for information comprises a request for allele frequency for one or more alleles. The request for information can be a query submitted to the risk assessment system directly, or can be submitted to a database of genetic sequences and intercepted by, diverted to, or re-routed to the risk assessment system as a security measure. The inquirer can be a person submitting a request via a local or remote user interface, or can be a computer or other automated or computerized entity that is programmed or otherwise directed to query the database of genetic information. The request may be submitted either locally or remotely, and can be made via wireless and/or wired communication.

With the request for allele frequency for one or more alleles, the allele database generator 240 updates allele database 280. According to an embodiment, the request frequency for each of the one or more alleles identified in the received request for information is increased to reflect the latest request. Referring to Table 1, for example, if allele j is queried, the index of every genetic sequence containing allele j is changed to "1" while the index of ever genetic sequence that doesn't contain allele j remains at "0."

According to an embodiment, system 200 comprises an inquirer database generator 250, which may be a processor, a component of one or more processors, and/or a software algorithm. Inquirer database generator 250 generates inquirer database 290, which includes allele request information about a plurality of inquirers, and information about allele frequency information previously requested by each of the inquirers. Inquirer database 290 may be a single local or remote database, or may comprise multiple databases.

The information about inquirers stored within the inquirer database can include any identifying information about an individual or entity, real or automated, submitting a query to the risk assessment system. The system may collect identifying information such as an IP address, email address, name, phone number, coordinates or location, address, institutional or research facility association, credentials, and/or any other identifying or potentially identifying information.

The allele frequency information stored within the inquirer database can include information about the occurrence frequency of one or more alleles in a collection of genetic sequences. The inquirer database further includes information about allele frequency information previously requested by inquirers. The inquirer database tracks, using any method, the alleles requested by an inquirer, which is utilized for subsequent risk assessment. The information provided in Tables 2 and 4 are just a few examples of the type of information, and structure of information, than can be included in inquirer database 290.

According to an embodiment, inquirer database generator 250 also updates inquirer database 290 in response to a request for information from an inquirer. The request for information comprises a request for allele frequency for one or more alleles, as well as information about the identity of the requesting or querying inquirer. For example, the request frequency for each of the one or more alleles identified in the received request for information, for the requesting or querying inquirer, is increased to reflect the latest request. Referring to Table 2, for example, if inquirer j queries allele i, for example, the index for inquirer j at allele i is changed to "1" to reflect the request.

According to an embodiment, system 200 comprises a risk analyzer 260, which may be a processor, a component of one or more processors, and/or a software algorithm. Risk analyzer 260 calculates an allele risk score based on the updated allele database, calculates an inquirer risk score based on the updated inquirer database, and/or assesses the risk associated with a received request for information from the database of genetic information based at least in part on the calculated allele risk score and the calculated inquirer risk score.

The allele risk score is based on the frequency of the allele among all the sequences in the allele database. For example, the risk analyzer 260 determines the allele risk score based on the requested information, allele frequency, and/or history of requests for that particular sequence. According to just one embodiment, the risk level for a genetic sequence in the database is calculated using Equation 1, described in detail herein. The allele risk score may be generated and/or stored as described in conjunction with Table 3, among many other methods of generation and storage.

According to an embodiment, the allele risk score or risk level may be modified based on one or more other pieces of internal and/or external information. For example, if information about a genetic sequence stored within the database of genetic information is available publicly or in another accessible database, the risk level for that genetic sequence is increased accordingly, as re-identification may be easier.

The inquirer risk score is based on the number of alleles requested by the inquirer, as well as on the frequency of those alleles in the database. According to just one embodiment, the risk level for a particular inquirer in the inquirer database is calculated using Equation 2, described in detail herein. The risk level for an inquirer may be generated and/or stored as described in conjunction with Table 4, among many other methods of generation and storage.

According to an embodiment, the inquirer risk level may be modified based on one or more other pieces of internal and/or external information. For example, if information about an inquirer within the inquirer database is known, such as a high risk factor associated with an inquirer, the risk level for that inquirer may be increased accordingly. According to another embodiment, if the inquirer is new or unknown, or has not accessed or queried the database within a predetermined timeframe, the risk level for that inquirer may be increased accordingly. There may also be situations where the risk level for an inquirer is decreased, such as with two-factor verification, biometric verification, or other verification methods that increase the likelihood that an inquirer is valid and unlikely to be attempting to re-identify genetic sequences in the database.

Risk analyzer 260 assesses the risk associated with a received request for information from the database of genetic information based at least in part on the calculated allele risk score and the calculated inquirer risk score. For example, the sum of the calculated allele risk score and calculated inquirer risk score can comprise the risk associated with the received request. The sum may be the sum of the output of Equation 1 and Equation 2, among many other possible methods. The calculated risk may be compared to one or more thresholds to determine the risk level as described or otherwise envisioned herein.

System 200 may implement the assessed risk by allowing or denying the received request for genetic information from the inquirer. For example, the risk analyzer 260 may provide the results of the risk assessment to the system, or risk analyzer 260 may allow or deny a received request based on the risk assessment. For example, if the assessed risk is determined by the risk assessment system to be too great, the system denies the received request. If the assessed risk is determined by the risk assessment system to be acceptable, the system grants the received request. The system may request additional information from the inquirer in response to an assessed risk. For example risk analyzer 260 may direct the system to request information about the identity of the inquirer if the inquirer cannot be identified, or if the inquirer is identified as a high-risk inquirer, or if the inquirer is requesting information that triggers a high allele risk score.

According to an embodiment, system 200 comprises a report generator 270, which may be a processor, a component of one or more processors, and/or a software algorithm. Report generator 270 is configured to generate a report of the risk assessment performed by system 200. The report may be provided to a user via user interface 210, and/or through any other system, device, mechanism, or method for reporting. System 200 may also be configured to generate a printed report of the risk assessment performed by system 200. A report may include information about the allele(s) requested, the inquirer's identity, the calculated allele risk score and inquirer risk score, the assessed risk level, time and date, and/or any other information. Reporting may be based in whole or in part on the assessed risk level. For example, reporting may be provided for every request, or may only be provided in response to high-risk requests or inquirers, among many other options.

According to an embodiment, the methods and systems described or otherwise envisioned herein for assessing the risk associated with a request for information about allele frequency data from a database of genetic sequences significantly improve the security of the genetic sequence data sharing system. This saves computing power and improves efficiency of the system.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of".

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for assessing risk associated with a request from an inquirer for allele frequency from a database of genetic data, comprising:
   generating an allele database comprising allele frequency information and request frequency information for each of a plurality of alleles, wherein the allele frequency information is extracted from a plurality of genetic sequences, and wherein the request frequency information comprises, for each of the plurality of genetic sequences, a count of previous requests for information about each of the plurality of alleles found within a respective genetic sequence;
   generating an inquirer database comprising allele request information about a plurality of inquirers, wherein the allele request information comprises information about allele frequency information previously requested by each of a plurality of inquirers;
   receiving a request for genetic data from an inquirer, comprising a request for allele frequency for one or more alleles and an identifier of the inquirer;
   updating in the allele database, for each of the plurality of genetic sequences comprising the one or more alleles, the request frequency information based on the received request;
   updating in the inquirer database, based on the received inquirer identifier, the allele request information for the requesting inquirer;
   calculating an allele risk score based on the updated allele database wherein the allele risk score is calculated using the equation:

$$Ri = \sum_{j=1}^{n} \text{Index}(i, j)/F(j)$$

where Ri is the risk level of the genetic sequence, n is the number of rare alleles, F(j) is the frequency of allele j, and Index (i,j) is the number of requests for allele j for genetic sequence i;
   calculating an inquirer risk score based on the updated inquirer database; and
   assessing, based on the allele risk score and the inquirer risk score, a risk associated with the received request.

2. The method of claim 1, wherein the step of assessing a risk associated with the received request comprises the steps of:
   summing the calculated allele risk score and inquirer risk score to generate a total risk assessment score; and
   comparing the total risk assessment score to a predetermined threshold.

3. The method of claim 1, further comprising the step of allowing the request for genetic data from the inquirer if the risk associated with the received request is assessed to be below a predetermined threshold.

4. The method of claim 1, further comprising the step of denying the request for genetic data from the inquirer if the risk associated with the received request is assessed to be above a predetermined threshold.

5. The method of claim 1, further comprising the step of reporting the risk associated with the received request.

6. The method of claim 1, further comprising the step of requesting additional identifying information from the inquirer.

7. A risk assessment system configured to assess risk associated with a request from an inquirer for allele frequency from a database of genetic data, comprising:
- an allele database comprising allele frequency information and request frequency information for each of a plurality of alleles, wherein the allele frequency information is extracted from a plurality of genetic sequences, and wherein the request frequency information comprises, for each of the plurality of genetic sequences, a count of previous requests for information about each of the plurality of alleles found within a respective genetic sequence;
- an inquirer database comprising allele request information about a plurality of inquirers, wherein the allele request information comprises information about allele frequency information previously requested by each of a plurality of inquirers; and
- a processor configured to receive a request for genetic data from an inquirer, comprising a request for allele frequency for one or more alleles and an identifier of the inquirer, the processor comprising:
  - an allele database generator configured to update, in the allele database for each of the plurality of genetic sequences comprising the one or more alleles, the request frequency information based on the received request;
  - an inquirer database generator configured to update, in the inquirer database based on the received inquirer identifier, the allele request information for the requesting inquirer; and
  - a risk analyzer configured to:
    (i) calculate an allele risk score based on the updated allele database, wherein the allele risk score is calculated using the equation:

$$Ri = \sum_{j=1}^{n} \text{Index}(i, j)/F(j)$$

where Ri is the risk level of the genetic sequence, n is the number of rare alleles, F(j) is the frequency of allele j, and Index (i,j) is the number of requests for allele j for genetic sequence i;
    (ii) calculate an inquirer risk score based on the updated inquirer database; and
    (iii) assess, based on the allele risk score and the inquirer risk score, a risk associated with the received request.

8. The risk assessment system of claim 7, further comprising a user interface configured to report the assessed risk.

9. The risk assessment system of claim 7, wherein assessing the risk associated with the received request comprises summing the calculated allele risk score and inquirer risk score to generate a total risk assessment score, and comparing the total risk assessment score to a predetermined threshold.

10. The risk assessment system of claim 7, wherein the system is configured to allow the request for genetic data from the inquirer if the risk associated with the received request is assessed to be below a predetermined threshold.

11. The risk assessment system of claim 7, wherein the system is configured to deny the request for genetic data from the inquirer if the risk associated with the received request is assessed to be above a predetermined threshold.

12. The risk assessment system of claim 7, wherein the system is configured to report the risk associated with the received request.

13. The risk assessment system of claim 7, wherein the system is risk analyzer is further configured to request additional identifying information from the inquirer.

14. A method for assessing risk associated with a request from an inquirer for allele frequency from a database of genetic data, comprising:
- generating an allele database comprising allele frequency information and request frequency information for each of a plurality of alleles, wherein the allele frequency information is extracted from a plurality of genetic sequences, and wherein the request frequency information comprises, for each of the plurality of genetic sequences, a count of previous requests for information about each of the plurality of alleles found within a respective genetic sequence;
- generating an inquirer database comprising allele request information about a plurality of inquirers, wherein the allele request information comprises information about allele frequency information previously requested by each of a plurality of inquirers;
- receiving a request for genetic data from an inquirer, comprising a request for allele frequency for one or more alleles and an identifier of the inquirer;
- updating in the allele database, for each of the plurality of genetic sequences comprising the one or more alleles, the request frequency information based on the received request;
- updating in the inquirer database, based on the received inquirer identifier, the allele request information for the requesting inquirer;
- calculating an allele risk score based on the updated allele database;
- calculating an inquirer risk score based on the updated inquirer database, wherein the inquirer risk score is calculated using the equation:

$$Dj = \sum_{k=1}^{m} \left( \sum_{i=1}^{n} (\text{Index}(i, j)/Fi) \right) Rk$$

where Dj is the risk level for an inquirer j, m is the genetic sequence, n is the number of rare alleles, Index (i,j) is the number of requests for allele j for genetic sequence i, F(i) is the frequency of allele i, and Rk is the risk level; and
- assessing, based on the allele risk score and the inquirer risk score, a risk associated with the received request.

15. A risk assessment system configured to assess risk associated with a request from an inquirer for allele frequency from a database of genetic data, comprising:

an allele database comprising allele frequency information and request frequency information for each of a plurality of alleles, wherein the allele frequency information is extracted from a plurality of genetic sequences, and wherein the request frequency information comprises, for each of the plurality of genetic sequences, a count of previous requests for information about each of the plurality of alleles found within a respective genetic sequence;

an inquirer database comprising allele request information about a plurality of inquirers, wherein the allele request information comprises information about allele frequency information previously requested by each of a plurality of inquirers; and a processor configured to receive a request for genetic data from an inquirer, comprising a request for allele frequency for one or more alleles and an identifier of the inquirer, the processor comprising:

an allele database generator configured to update, in the allele database for each of the plurality of genetic sequences comprising the one or more alleles, the request frequency information based on the received request;

an inquirer database generator configured to update, in the inquirer database based on the received inquirer identifier, the allele request information for the requesting inquirer; and a risk analyzer configured to:

(i) calculate an allele risk score based on the updated allele database;

(ii) calculate an inquirer risk score based on the updated inquirer database, wherein the inquirer risk score is calculated using the equation:

$$Dj = \sum_{k=1}^{m} \left( \sum_{i=1}^{n} (\text{Index}(i,j)/Fi) \right) Rk$$

where Dj is the risk level for an inquirer j, m is the genetic sequence, n is the number of rare alleles, Index (i,j) is the number of requests for allele j for genetic sequence i, F(i) is the frequency of allele i, and Rk is the risk level; and (iii) assess, based on the allele risk score and the inquirer risk score, a risk associated with the received request.

\* \* \* \* \*